United States Patent [19]

Scrudto

[11] Patent Number: 4,762,009
[45] Date of Patent: Aug. 9, 1988

[54] IN-SITU INTEGRATED SUSPENDED SEDIMENT STREAM SAMPLER

[75] Inventor: Ronald J. Scrudto, Oswego, N.Y.

[73] Assignee: Research Foundation of State University of New York, Albany, N.Y.

[21] Appl. No.: 21,797

[22] Filed: Mar. 4, 1987

[51] Int. Cl.⁴ .......................... G01N 1/20; G01N 1/18
[52] U.S. Cl. ................ 73/863.52; 73/863.21; 73/863.23; 73/863.43; 73/863.58; 73/864.51
[58] Field of Search ........... 73/863.21, 863.22, 863.23, 73/863.24, 863.25, 863.41, 863.43, 863.51, 863.52, 863.58, 863.61

[56] References Cited

U.S. PATENT DOCUMENTS

| | | | |
|---|---|---|---|
| 2,400,465 | 5/1946 | Hammel | 73/863.21 |
| 2,446,487 | 8/1948 | Henry | 73/863.21 X |
| 3,400,575 | 9/1968 | Madden | 73/863.58 X |
| 4,167,117 | 9/1979 | Stokley et al. | 73/803.61 X |
| 4,343,199 | 8/1982 | Sunna | 73/863.43 |
| 4,699,013 | 10/1987 | Kroner | 73/863.23 |

OTHER PUBLICATIONS

National Handbook of Recommended Methods for Water-Data Acquisition-1977, pp. i-1 through i-3 Revision 7/80 and pp. 3-17 through 3-24 of 6/78 version, Dept. of Interior.

Primary Examiner—Tom Noland
Attorney, Agent, or Firm—Heslin & Rothenberg

[57] ABSTRACT

An in-situ integrated sampler relies upon the natural sedimentation process to continuously collect suspended sediment from a flowing stream over extended time periods. An upstream facing funnel captures a portion of the flowing stream and directs it into a sedimentation chamber where the flow is slowed sufficiently to induce settling of sediment. A receptacle disposed within the chamber collects settled sediment and apertures in a base member allow excess water to escape from the chamber. A stake mounted in the stream bed can be employed to orient the sampler and position it at a desired depth.

20 Claims, 3 Drawing Sheets

IN-SITU INTEGRATED SUSPENDED SEDIMENT STREAM SAMPLER

GOVERNMENT RIGHTS

This invention was made with Government support under Grant No. NO1-CM-27570 under the National Sea Grant College program, awarded by the United States Department of Commerce. The Government has certain rights in this invention.

BACKGROUND OF THE INVENTION

1. Technical Field

This invention relates generally to the field of water quality analysis and geochemical prospecting, and more specifically to an in-situ sampler for collecting suspended stream sediment over extended time periods.

2. Background Art

Over the years a variety of samplers and procedures have been developed and used for sampling suspended and bottom sediment. In general, the requisites for sampling suspended or fluvial sediment are different from those for sampling bottom sediment.

Suspended sediment in streams is sampled for a variety of purposes. In general, the intent is to supply samples for analyses to provide information on the quantity, i.e. concentration, and on the physical and chemical characteristics of the suspended sediment. Sorptive characteristics of suspended sediments have been recognized as an important process in the transport of natural and anthropogenic trace constituents. Suspended sediments have been used extensively in geochemical mineral exploration. They are also becoming increasingly recognized as important transporters of trace organic and inorganic contaminants in streams, lakes and marine environments.

Prior art suspended sediment samplers can be categorized into three classes—integrating samplers, instantaneous samplers and pumping samplers. Integrating samplers accumulate a water-sediment mixture over a period of time by withdrawing water and associated suspended sediment from the ambient flow through a relatively small nozzle. Instantaneous or grab samplers essentially trap a volume of the water-sediment mixture by instantaneously closing off the ends of a flow-through chamber. Pumping samplers withdraw a mixture of water and suspended sediment through an intake by a pumping action. Generally, passive integrating samplers are preferred because they obtain a water-sediment mixture from a long filament of flow, can sample at more than one point, and require no energy input or complicated velocity sensing and adjusting apparatus.

In the past, a variety of hand-held and cable and reel integrated samplers have been used to assess suspended sediment concentrations in streams. These samplers were generally designed to sample relatively small quantities of water, usually less than one liter and therefore have limited application for environmental and geochemical exploration sampling.

Various filtering apparati have been used to separate suspended sediments which rely on collection of a water sample and then separating the suspended fraction by some mechanical process. Commonly, water samples are collected and either filtered at the site or the suspended material is separated at the laboratory. In either case, whole water samples are collected within short term periods and therefore reflect instantaneous or short term stream events or episodes. Continuous sampling pumps, coupled to an on-site centrifuge are able to sample large volumes of water for extended periods. This approach, however, requires an electrical source which limits application to relatively accessible areas, and is also personnel intensive requiring continuous monitoring.

SUMMARY OF THE INVENTION

In accordance with the present invention, an improved stream sampler capable of continuous collection of suspended stream sediment over extended time periods is provided, which overcomes many of the limitations of the prior art. The integrated sampler of the present invention is passive and relies on natural sedimentation principles and therefore requires neither ancillary operating power nor conventional filtration or centrifugation to remove the suspended fraction from collected water samples. The sampler is also lightweight, self-actuated, simple and inexpensive to construct, readily deployed and serviced, and can be used in remote areas, unattended, over extended time periods for environmental or geochemical sampling.

The sampler of the present invention is designed to capture a portion of a flowing stream containing sediment and direct said portion into a sedimentation chamber. In this chamber, the stream flow is slowed to induce settling of suspended sediment and the settled sediment is collected. Apertures in the chamber allow for discharge of water and accordingly sampling of the stream over an extended period of time. In a preferred form, the sampler includes a funnel to capture a portion of the flowing stream, a cylindrical housing having a water impermeable top member and a perforated base member for defining the sedimentation chamber, a receptacle in said chamber for collecting settled sediment and channeling means in said chamber for directing settling sediment into said receptacle. The outlet of the funnel is sized and the apertures in the base member are sized and positioned so as to reduce the flow in the chamber and induce sedimentation. The sampler is preferably constructed for ready disassembly, sample removal and cleaning. The receptacle for collecting settled sediment and other portions of the sampler may be made of inert material to avoid sample contamination. The receptacle can also accommodate a removable and replaceable beaker to minimize interruption of sampling, and a cross baffle to further inhibit flow if desired. The collecting funnel is preferably thread-mounted to the main body of the sampler allowing rapid change of funnel diameter.

The sampler may be positioned at any depth and oriented with the funnel facing upstream on a support rod secured, for example on or in the stream bed. The sampler is preferably supported such that it may be readily vertically repositioned or removed from the support rod. The sampler of the present invention can be used singly or in groups to determine lateral and vertical suspended sediment variations within a stream. The invention also encompasses the method of sampling advantageously implemented by the described hardware.

BRIEF DESCRIPTION OF THE DRAWINGS

These and other objects, features and advantages of the invention will be more readily understood from the following detailed description of illustrative embodiments when read in conjunction with the accompanying drawings in which.

DETAILED DESCRIPTION

Figure 1:
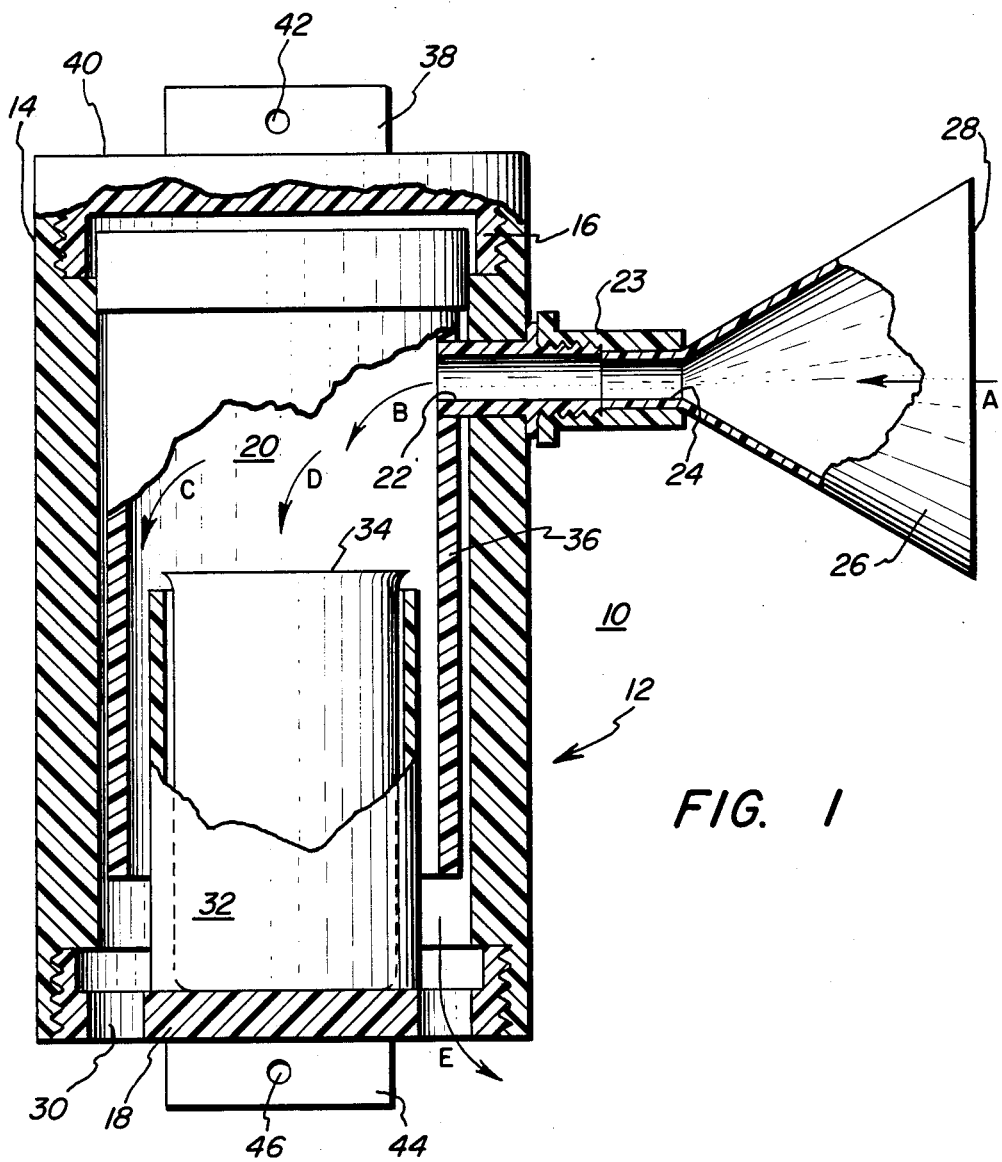
FIG. 1 is a vertical sectional view of a preferred embodiment of the sampler of the present invention.
Figure 2:
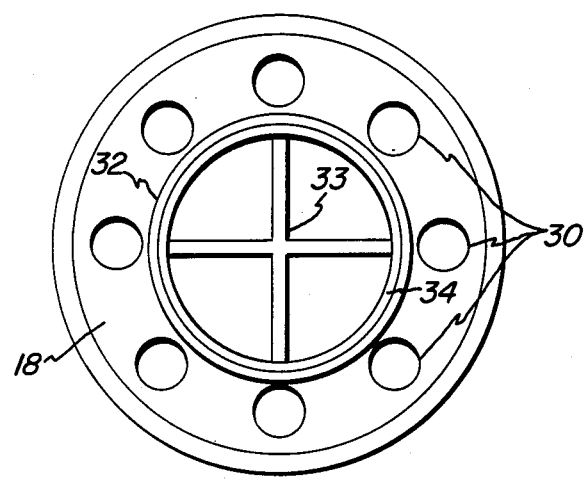
FIG. 2 is a top plan view of a base member of the sampler of FIG. 1.

Referring now to the figures, an in-situ integrated suspended sediment stream sampler 10, constructed in accordance with the principles of the invention, is depicted in FIG. 1. (For purposes of this description, the term "stream" is intended to encompass any flowing body of liquid, whether natural or man-made.) The sampler includes a main body or housing 12, preferably of cylindrical configuration. Housing 12 includes side walls 14, a top member 16 and a perforated base member 18. The interior of housing 12 comprises a reduced flow sedimentation chamber generally designated 20.

A hollow adaptor 22 extends through and out of side wall 14 and is secured thereto by glue or other suitable means. The exterior surface of adaptor 22 is threaded to threadably engage cooperating threads on the interior of one end of a mounting sleeve 23. The other end of sleeve 23 frictionally engages the neck portion 24 of a funnel 26. In use, sampler 10 is oriented so that the mouth 28 of funnel 26 faces upstream to capture a portion of a flowing stream containing sediment. Arrow A indicates the direction of stream flow. The thread mounting of funnel 26 to main body 12 allows rapid exchange of funnels with different diameter openings. Larger diameter funnels may be more desirable for streams with small suspended sediment concentrations and/or low flows.

The side walls 14 and top member 16 of housing 12 are generally water impermeable while base member 18 is provided with a series of circumferentially spaced water discharge apertures 30. The number, size, and location of apertures 30 are selected, in conjunction with the restricted size of the outlet of funnel 26 to reduce the flow of water in chamber 20 to a level that permits settling of suspended sediment within this chamber. A receptacle 32 for collecting settled sediment is centrally mounted to base member 18. Receptacle 30 preferably is cylindrically shaped and extends substantially to the inner edges of appertures 30. To guard against contamination of the collected sample, receptacle 32 can advantageously be constructed of glass or other inert material. If desired, a beaker 34 made of glass, plastic or other suitable material may be inserted inside receptacle 32, which beaker can be readily removed and replaced to minimize interruption of sampling. A removable, axially extending cross baffle 33 preferably made of inert material can be advantageously employed in beaker 34 to further reduce flow therein.

Located in between receptacle 32 and side walls 14 of housing 12 is an intermediate channeling means 36 which serves to channel most of the settling sediment into receptacle 32. Channeling means 36 preferably takes the form of a hollow, concentric cylindrical tube secured near its upper end to side walls 14. Channeling means 36 is sized so as to be spaced from side walls 14 and preferably to be substantially aligned with the outer edges of apertures 30. The lower end of channeling means 36 terminates short of base member 18 and is open allowing water passage therethrough. As shown, nipple 22 connected to neck portion 24 of funnel 26 extends through channeling means 36 so that incoming sediment containing water is directed in the general direction of arrows B and C with sediment settling as shown by arrow D in receptacle 32 and excess water flowing out of the sampler through discharge apertures 30 as shown by arrow E.

Figure 3:
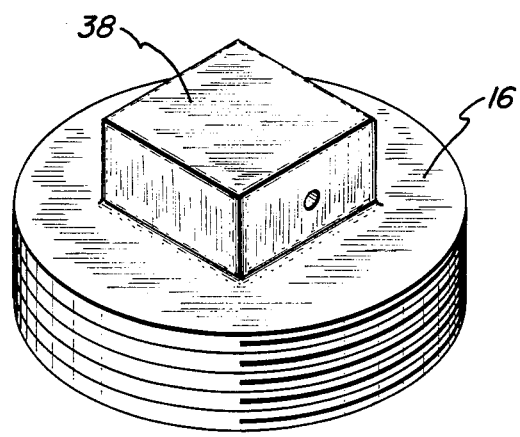
FIG. 3 is a perspective view of the top member of the sampler of FIG. 1.

As shown in FIG. 3, top member 16 preferably has a circular cross section with external threads for threadable engagement with matching threads provided on the interior of the top portion of side walls 14. A boss or protruding external cap 38 mounted on the exterior surface 40 of top member 16 provides a convenient handle for screwing in or unscrewing the top member 16 with respect to the housing. Cap 38 has a square cross section or other configuration which allows easy hand gripping and torque application. An aperture 42 extending through cap 38 provides a convenient channel for receiving a supporting rod, as more fully described hereinafter. Threaded base member 18 is also threadedly mounted to the side walls 14 of the housing and can be provided with a similar end cap 44 also having a through hole 46. The thread mounting of top member 16 and base member 18 allow ready disassembly of the sampler for ease of sample removal and cleaning.

Figure 4:
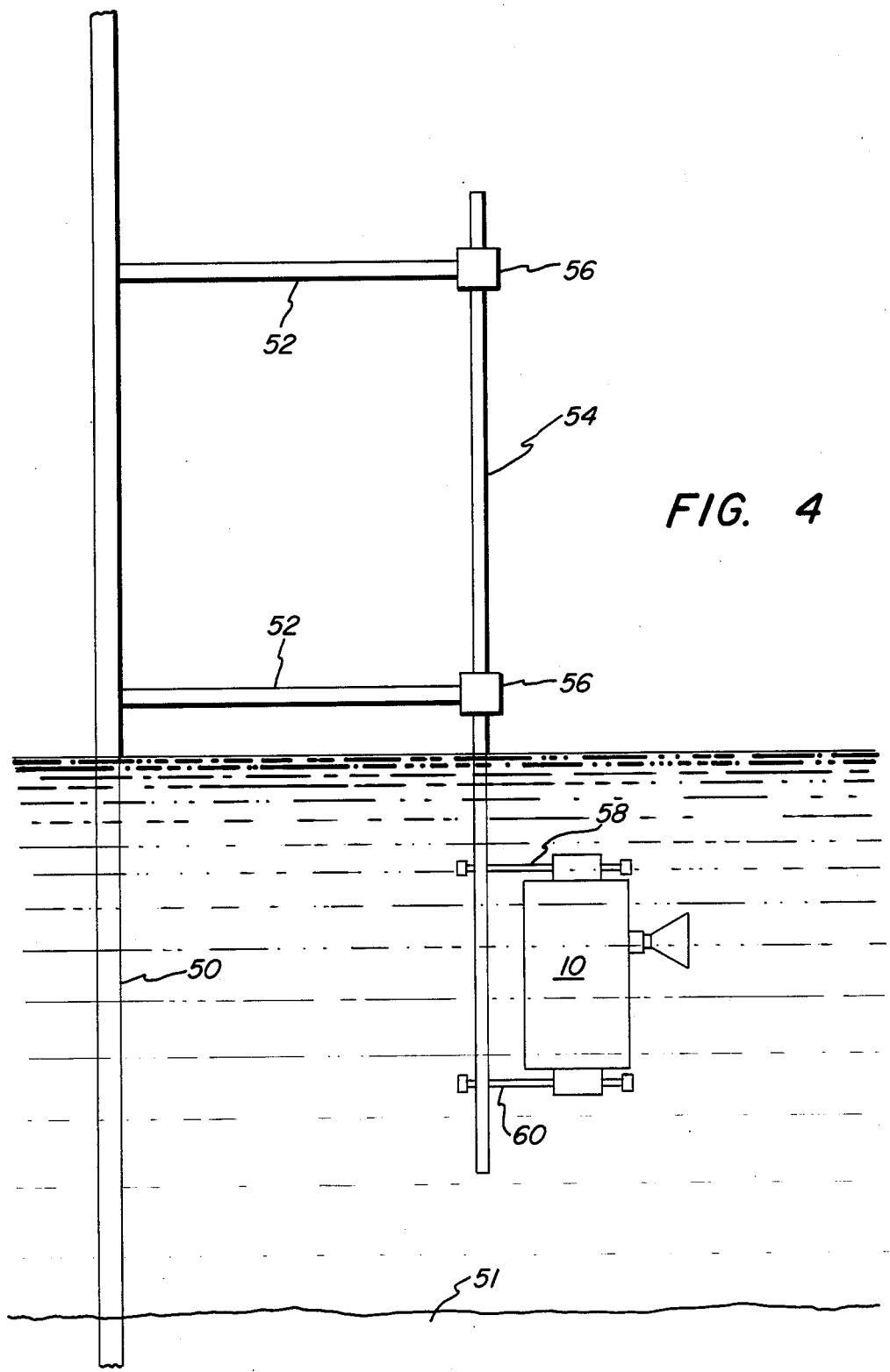
FIG. 4 is an elevational view of a support structure for the sampler of FIG. 1.

Sampler 10 can be supported at a desired depth in flowing water by a support stake 50 mounted on or secured in stream bed 51, as shown in FIG. 4. Rods 52 extend generally horizontally from anchoring stake 50 to an adjustable positioning rod 54 which supports the sampler 10. U-shaped clamps or other suitable securing means 56 are attached to the distal ends of rods 52 and allow both vertical adjustment and ready removal of positioning rod 54 and the connected sampler 10. Sampler 10 is secured to positioning rod 54 by an upper threaded rod 58 and a lower threaded rod 60. Rod 58 extends through aperture 42 of top cap 38 while rod 50 extends through aperture 46 of bottom cap 44. Nuts threadably engaged with rods 58 and 60 can be used to position and secure sampler 10 to these rods.

The sampler of this invention can be used singly or in lateral or vertical nests. More than one sampler can be secured on positioning rod 54 to collect samples from varying depths. Similarly, a lateral array of samplers can be used to collect samples from within different areas of the stream profile. Samplers can also be located at various sites providing a means of determining sources of stream contaminants or metals of economic interest.

The sampler mounting system described was designed for shallow water (less than 1.5 m) and is best suited for positioning in alluvium, although it can be used in areas where bedrock joints or fractures enable wedging of the supporting stake. Other support structures for maintaining the sampler at a desired depth and with an upstream orientation in any body of flowing water can of course be used.

The operating principle of the sampler of the present invention is to funnel suspended sediment into the sedimentation chamber where flow is reduced sufficiently to allow sedimentation, with the settled sediment being collected in the receptacle within the chamber. A prototype sampler was constructed of poly vinyl chloride with the sediment collecting receptacle made of clear cellulose acetate butylate. The sediment receptacle had an inner diameter of about 5.8 cm, the intermediate cylindrical channeling means an inner diameter of about 7.6 cm and the housing a 10 cm inner diameter. The discharge apertures had a diameter of about 1.2 cm. The prototype was field tested by positioning it at about 0.75 m water depth in a running upstate New York stream with the funnel opening facing upstream at about 0.1 m above the stream bottom. Flow of the stream varied from about 3.5–5.0 m/sec. and the suspended sediment varied from 2.0–5.0 mg/l during the seven day test period. The sampler collected 1.2 dry grams of suspended sediment during this test period indicating that, if 100% of the suspended fraction was trapped by the sampler, between 600 and 240 liters of water passed through the sampler during the test period. A more realistic sampling efficiency of 10% suggests the sampler processed 6,000–2,400 liters of water during the seven day period.

From the foregoing, it will be appreciated that a suspended sediment stream sampler has been described which is capable of continuously sampling a flowing stream over an extended period of time. The sampler of the present invention collects sediment rather than a sediment-water mixture collected by prior art integrated samplers and therefore eliminates the need for subsequent filtering or centrifugation of the sample. This sampler is passive, self-activated and can be readily deployed and used without any ancillary power or accessories, at remote and otherwise inaccessible sites. The sampler is simple, inexpensive, lightweight and easily serviced and cleaned. It affords an efficient, independent sampling technique, relying upon the natural sedimentation process and facilitating collection of integrated samples. Although specifically designed to collect suspended sediments for environmental monitoring, the sampler can also be advantageously utilized to determine lateral and vertical suspended sediment variations within a stream and for geochemical prospecting. The sampler is simple to set up and can be left unattended for extended periods of time.

Although a preferred embodiment of the sampler has been described and depicted, it will be readily apparent to those skilled in this art that numerous modifications, substitutions, and the like may be made without departing from the spirit of the invention. By way of example, other funnel mounting mechanisms or sampler supporting structures can be employed. The invention is intended to encompass all such variations which fall within the scope of the appended claims.

What is claimed is:

1. An in-situ integrated suspended sediment stream sampler, comprising:
   upstream facing capture means for capturing flowing water containing suspended sediment;
   container means defining a hollow sedimentation chamber for receiving the captured sediment-containing water and slowing the flow therethrough so as to induce settling of the sediment within said chamber, said container means including a housing having side walls, a water impermeable top member, and a base member which is at least partially water permeable to allow water to escape through said base member; and
   open top receptacle means located within said chamber for receiving and collecting settled sediment.

2. The sampler of claim 1 wherein said base member is perforated.

3. The sampler of claim 2 wherein said perforated base member contains a plurality of circumferentially spaced water discharge apertures.

4. The sampler of claim 3 wherein said apertures are sized and positioned to assist in reducing the flow of water within said chamber.

5. The sampler of claim 4 wherein said capture means comprises a funnel, with a mouth of the funnel facing upstream and a neck of the funnel communicating with an aperture extending through a side wall of said housing.

6. The sampler of claim 5 wherein the funnel is mounted to said side wall such that the funnel may be readily removed and replaced by another funnel of different mouth diameter.

7. The sampler of claim 6 wherein said container means further comprises intermediate channeling means for receiving sediment containing water from said funnel and serving to channel settling sediment into said receptacle means.

8. The sampler of claim 7 wherein said channeling means is secured to the side walls of the housing and extends generally parallel to said side walls to a point spaced from the base member of the housing.

9. The sampler of claim 8 wherein the channeling means circumscribes the receptacle means.

10. The sampler of claim 9 wherein the housing, channeling means and receptacle means are cylindrical and concentric.

11. The sampler of claim 10 wherein said receptacle means is constructed of inert material to guard against contamination of the settled sediment.

12. The sampler of claim 10 wherein the receptacle means is secured to the bottom member, and further comprising a removable beaker inserted into the receptacle means.

13. The sampler of claim 12, further comprising a cross baffle located in said beaker for further reducing flow in the beaker.

14. The sampler of claim 10 in combination with support means for supporting said sampler at a desired stream depth and in an upstream facing orientation.

15. The apparatus of claim 14 wherein said support means comprises a support stake insertable in the stream bed, a positioning rod for mounting the sampler, and securing means for securing the positioning rod to said support stake, said securing means facilitating ready removal and vertical positioning of the positioning rod and the sampler mounted thereto.

16. The sampler of claim 10 wherein the top member and base member are threadably mounted to the side walls of the housing to facilitate disassembly and cleaning of the sampler.

17. The sampler of claim 16 wherein the top member and base member are each provided with an external protruding cap member to facilitate threading and unthreading of the respective top member and base member to the housing.

18. The sampler of claim 17 wherein each cap member has an exterior configuration designed to facilitate rotation by hand.

19. The sampler of claim 18 wherein each cap member further comprises means for cooperatively engaging a support member.

20. The sampler of claim 19 wherein each cap member has a substantially square cross section and an aperture passing therethrough for receiving a support rod.

* * * * *

UNITED STATES PATENT AND TRADEMARK OFFICE
CERTIFICATE OF CORRECTION

PATENT NO. : 4,762,009

DATED : August 9, 1988

INVENTOR(S) : Ronald J. Scrudato

It is certified that error appears in the above-identified patent and that said Letters Patent is hereby corrected as shown below:

Page 1, Inventor: Ronald J. Scrudto, Oswego, N.Y.
should read Inventor: Ronald J. Scrudato, Oswego, N.Y.
Item [19], "Scrudto" should read -- Scrudato --.

Signed and Sealed this

Seventeenth Day of January, 1989

*Attest:*

DONALD J. QUIGG

*Attesting Officer*  *Commissioner of Patents and Trademarks*